(12) United States Patent
Bickmore, Jr. et al.

(10) Patent No.: US 7,315,376 B2
(45) Date of Patent: Jan. 1, 2008

(54) FLUORESCENCE DETECTION SYSTEM

(75) Inventors: William D. Bickmore, Jr., St. George, UT (US); Danvern Ray Roberts, Las Vegas, NV (US)

(73) Assignee: Advanced Molecular Systems, LLC, St. George, UT (US)

( * ) Notice: Subject to any disclaimer, the term of this patent is extended or adjusted under 35 U.S.C. 154(b) by 321 days.

(21) Appl. No.: 11/031,526

(22) Filed: Jan. 7, 2005

(65) Prior Publication Data

US 2006/0152727 A1 Jul. 13, 2006

(51) Int. Cl.
*G01N 21/25* (2006.01)
(52) U.S. Cl. .................................................. 356/417
(58) Field of Classification Search ............... None
See application file for complete search history.

(56) References Cited

U.S. PATENT DOCUMENTS

| | | | |
|---|---|---|---|
| 4,811,218 A | | 3/1989 | Hunkapiller et al. |
| 5,538,848 A | | 7/1996 | Livak et al. |
| 5,757,014 A | * | 5/1998 | Bruno et al. ............. 250/458.1 |
| 5,854,684 A | * | 12/1998 | Stabile et al. ................ 356/440 |
| 5,935,522 A | | 8/1999 | Swerdlow et al. |
| 5,935,524 A | * | 8/1999 | Bass et al. ................... 422/104 |
| 6,015,674 A | | 1/2000 | Woudenberg et al. |
| 6,027,695 A | * | 2/2000 | Oldenburg et al. .......... 422/102 |
| 6,174,670 B1 | | 1/2001 | Wittwer et al. |
| 6,369,893 B1 | | 4/2002 | Christel et al. |
| 6,399,397 B1 | * | 6/2002 | Zarling et al. ............... 436/172 |
| 6,597,450 B1 | | 7/2003 | Andrews et al. |
| 6,652,809 B1 | * | 11/2003 | Comley et al. ........... 422/82.05 |
| 6,814,934 B1 | | 11/2004 | Higuchi |
| 6,838,680 B2 | | 1/2005 | Maher et al. |
| 6,852,986 B1 | | 2/2005 | Lee et al. |
| 6,881,962 B2 | | 4/2005 | Kamijo et al. |
| 6,912,050 B2 | | 6/2005 | Inberg |
| 6,914,677 B2 | | 7/2005 | Mader et al. |
| 7,119,345 B2 | * | 10/2006 | King ........................ 250/458.1 |
| 7,122,799 B2 | * | 10/2006 | Hsieh et al. ........... 250/339.12 |

(Continued)

OTHER PUBLICATIONS

Ioulia Rouzina and Victor A. Bloomfield; Force-Induced Melting of the DNA Double Helix; Feb. 2001; 882-893; vol. 80; University of Minnesota; St. Paul, Minnesota, US.

(Continued)

*Primary Examiner*—Gregory J. Toatley, Jr.
*Assistant Examiner*—Jonathan Skovholt
(74) *Attorney, Agent, or Firm*—Holme Roberts & Owen LLP

(57) ABSTRACT

Apparatus and methods for exciting and detecting fluorescence in samples are disclosed. In one embodiment, a sample holder for holding a plurality of samples is provided together with an optical manifold having an excitation source, a photo receiver, or both, for each of the plurality of samples. In another embodiment, the optical manifold contains only the excitation source or a photo receiver, and the other is associated with the sample holder. This system permits for rapid excitation and measurement of fluorescence without the use of moving parts and without any opto-mechanical or electronic disturbance. It exhibits an exceptional signal to noise ratio, which permits it to differentiate between very low level differences in fluorescence.

34 Claims, 5 Drawing Sheets

U.S. PATENT DOCUMENTS

2003/0013188 A1* 1/2003 Dumas .................... 435/288.4
2004/0043502 A1* 3/2004 Song et al. ................. 436/172
2004/0119974 A1* 6/2004 Bishop et al. ............. 356/317
2004/0178357 A1* 9/2004 King ....................... 250/458.1
2006/0019274 A1   1/2006 Bickmore, Jr.

OTHER PUBLICATIONS

Ioulia Rouzina and Victor A. Bloomfield; Force-Induced Melting of the DNA Double Helix; Feb. 2001; 894-900; vol. 80; University of Minnesota; St. Paul, Minnesota, US.

* cited by examiner

FLUORESCENCE DETECTION SYSTEM

CROSS-REFERENCE TO RELATED APPLICATIONS

Not applicable.

BACKGROUND OF THE INVENTION

1. The Field of the Invention

The present invention is directed to a methods and apparatus for exciting fluorescent material and detecting fluorescence in a sample.

2. The Relevant Technology

Various optical detection systems have been developed for use in qualitative and quantitative measurements. One common system involves the use of fluorescent compounds as labels that are associated with targets, such as the reaction products of polymerase chain reaction (PCR) amplification.

Numerous chemical compounds have been identified that exhibit fluorescence when illuminated with light at a suitable excitation frequency. For example, fluorescein is excited by light at a wavelength of about 490 nm, and emits light at a wavelength of about 520 nm. The gap between the excitation and emission wavelengths allows observation and measurement of fluorescence either qualitatively or quantitatively by reference to the emission wavelength.

One conventional fluorescent reading system passes a light through a bandpass filter, which transmits light at the excitation wavelength, through a sample, through a second bandpass filter that transmits light at the emission wavelength, and to a detector. In this classical system, multiple samples are shuttled into place for sequential readings, such as through use of a carousel. In order to speed up the process, alternative stepping systems have been developed (for example, see U.S. Pat. No. 6,015,674) or multiple light emitting diodes have been provided together with a network of optical fibers to perform several tests simultaneously (see, for example, U.S. Pat. No. 6,597,450). Although these types of systems are useful, they produce opto-mechanical noise which reduces sensitivity of the system, and they require a significant amount of time to measure all of the samples due to the time it takes to move the optical system head to the samples, or the samples to the head. Fiber optic systems further suffer from the attenuation of a signal associated with the use of fiber optics, which also reduces sensitivity.

BRIEF SUMMARY OF THE INVENTION

The present invention provides apparatus and methods for exciting and detecting fluorescence in samples.

In one embodiment, a sample holder for holding a plurality of samples is provided together with an optical manifold having a separate excitation source and a separate photo receiver for each of the plurality of samples.

In another embodiment, the optical manifold contains only an excitation source, and the photo receiver is associated with the sample holder.

In another embodiment, the optical manifold contains only a photo receiver, and an excitation source is associated with the sample holder.

In another embodiment, no optical manifold is provided, and both the excitation source and the photo receiver are located in the sample holder.

The present invention permits rapid excitation and measurement of fluorescence without the use of moving parts and without any opto-mechanical or electronic disturbance. It exhibits an exceptional signal to noise ratio, which permits it to differentiate between very low level differences in fluorescence.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The present invention provides an optical system useful for measurement of small amounts of fluorescence in single samples or an array of samples, such as in a conventional 96 well plate. A feature of the invention is the lack of mechanical movement or sharing of optical components during excitation/emission, resulting in very rapid readings, and avoiding loss of sensitivity due to opto-mechanical movements.

Figure 1:
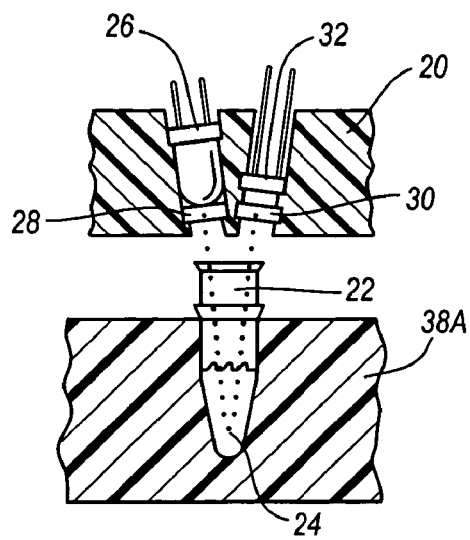
FIG. 1 is a schematic representation of an embodiment including an optical manifold, sample holder and photo receiver.

An embodiment of the present invention is depicted in FIG. 1, which illustrates one configuration for practicing the present invention. FIG. 1 illustrates the positioning of an optical manifold 20 in proximity to a sample vial 22 held by a sample well support 38A. Sample vial 22 contains a sample 24 which may contain a substance to be detected qualitatively or quantitatively using fluorescence.

Optical manifold 20 is provided with an excitation source 26 that generates light at the excitation frequency. An excitation bandpass filter 28 passes light at the excitation frequency.

Excitation source 26 and excitation bandpass filter 28 are arranged so that light at the excitation frequency will strike sample 24. An emission bandpass filter 30 is located over sample 24 so that it will be struck by emissions from fluorescent material in the sample. A suitable photo receiver 32 receives light passing through emission bandpass filter 30.

Although other configurations may be used, it is presently preferred that the excitation source and the photo receiver be set off-axis so as to form a ray trace which is primarily coincidental to targeted liquid in a PCR well. An offset of 7 degrees has been found suitable. Of course, those of ordinary skill will appreciate in view of the teachings herein that other configurations are possible.

Figure 2:
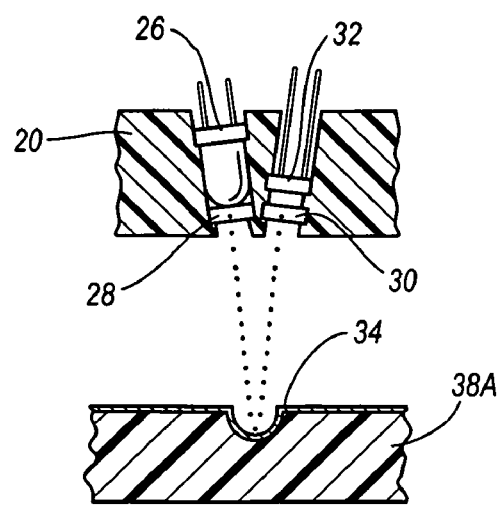
FIG. 2 is a schematic representation of another embodiment including an optical manifold, sample holder and photo receiver.

FIG. 2 illustrates a different approach for holding a sample. Unlike FIG. 1, which shows the use of a sample vial, FIG. 2 shows the use of a dimple 34 which can hold a suitable volume of sample. It will be apparent to one of ordinary skill in view of these teachings that other structures may be used in place of a dimple.

Figure 3:
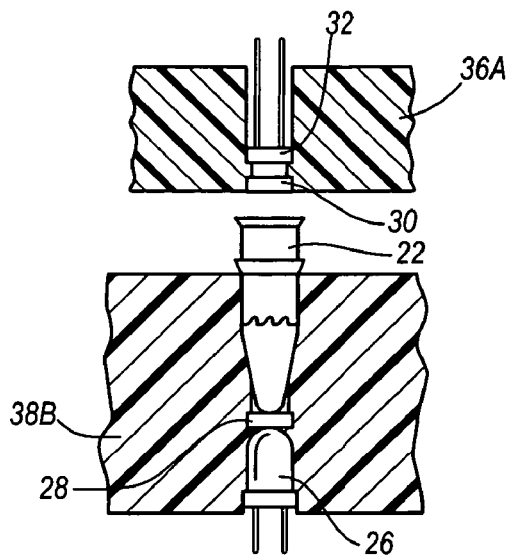
FIG. 3 is a schematic representation of another embodiment including an optical manifold, sample holder and photo receiver.

FIG. 3 illustrates an alternative geometric arrangement of the components of FIG. 1. In FIG. 3, manifold 36A supports a photo receiver 32 and a bandpass filter 32 over sample well 22, and sample well support 38B is fitted with excitation source 26 and excitation bandpass filter 28.

Figure 4:
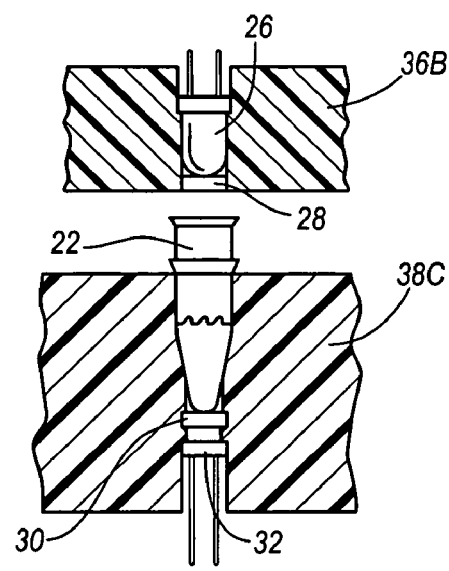
FIG. 4 is a schematic representation of another embodiment including an optical manifold, sample holder and photo receiver.

FIG. 4 is similar to FIG. 3, but the excitation source and excitation bandpass filter are located in manifold 36B, and emission bandpass filter 30 and photo receiver 32 are located in sample well support 38C.

Figure 5:
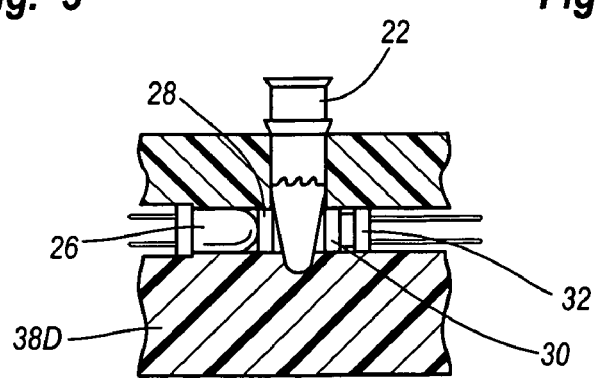
FIG. 5 depicts a sample holder having an excitation source and photo receiver incorporated therein.

FIG. 5 depicts an alternative embodiment of the invention omits the use of a separate optical manifold. FIG. 5 shows one manner of incorporating an excitation source 26 and a photo receiver 32 in sample well support 38D. As with other embodiments, the embodiment of FIG. 5 may also include excitation bandpass filter 26 and emission bandpass filter 30. Because of the cost of incorporating these components in the sample holder, it is preferred that the sample holder assembly be reusable, and to effect easy disposal of samples, it is preferred that the sample holder be configured to accept sample vials 22 rather than dimples or other non-disposable sample receptacle. In FIG. 5, the excitation source and photo receiver are depicted in-line with one another. One or ordinary skill will appreciate in view of the teachings herein that other configurations would also provide the benefits of the invention.

Suitable excitation sources include an LED and a laser diode. It is presently preferred that the excitation source provide high luminosity, preferably in the range of about 7000 to 25,000 millicandle power. It is also preferred that the excitation source have a dispersion beam less than about 20 degrees so as to provide efficient emission without the need for condensing optics.

Suitable photo receivers include cadmium sulfide photo resistors, PIN diodes, photo-transistors, or other devices capable of detecting light at the excitation frequency.

It will also be appreciated by one of ordinary skill in the art that there may be no need for a bandpass filter, or that other structures may be provided in place of a bandpass filter to remove unwanted light or if the illumination source is monochromatic at the desired wavelength.

It would be possible to add further structures, such as focusing optics, but it has been found in the configurations described above that no separate optics are typically necessary.

Figure 6:
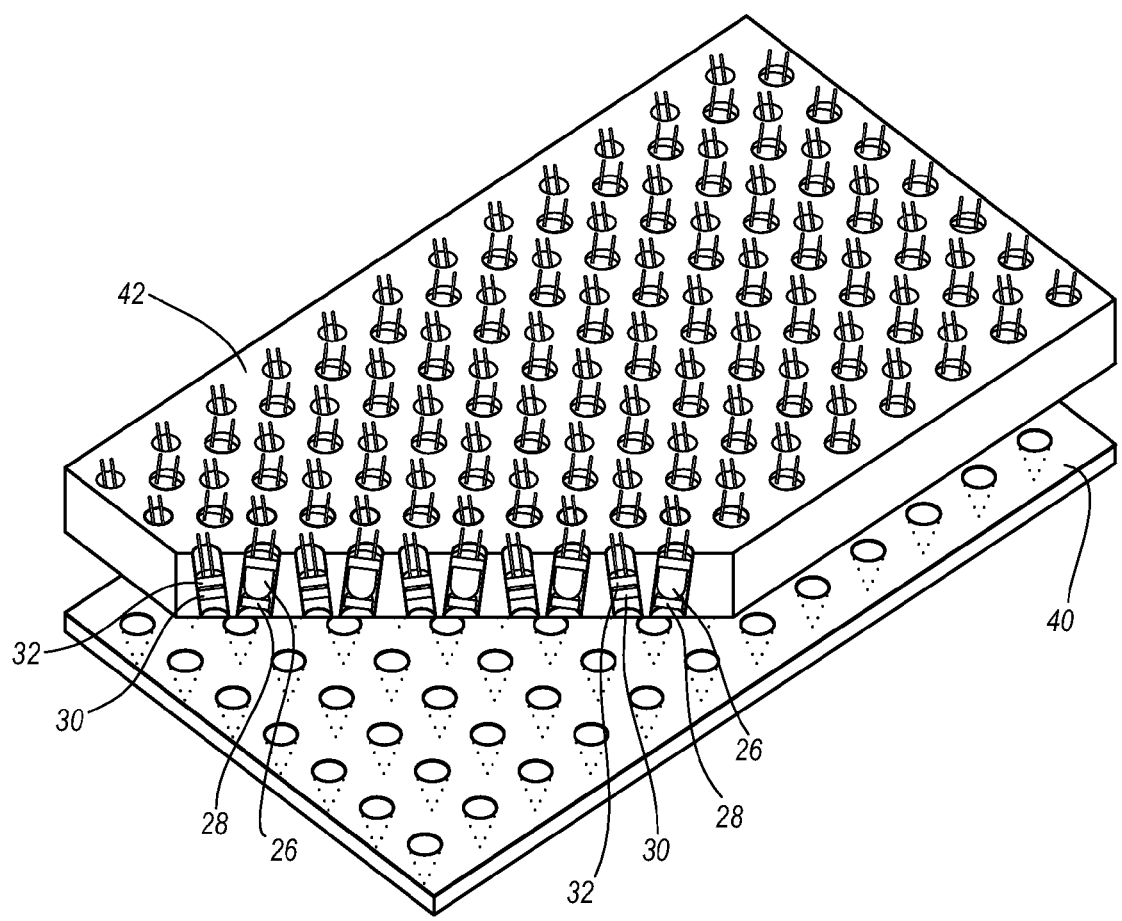
FIG. 6 depicts a sample holder having the configuration of a conventional 96 well plate, and an optical manifold having an excitation source and photo receiver associated with each of the 96 sample holders.

FIGS. 1-5 show various optical component configurations associated with a single sample. One of the advantages of the present invention is the ability to deal with a large number of samples simultaneously. FIG. 6 illustrates the use of the basic configuration of FIG. 1 for each sample well of a conventional 96 well plate 40. This is accomplished in FIG. 6 by providing a manifold 42 fitted with 96 separate combinations of excitation source 26, excitation bandpass filter 28, emission bandpass filter 30 and photo receiver 32, which are associated with the 96 sample wells. The configuration of FIG. 6 is suitable for use in connection with PCR or ELISA readers, or other multiple sample requirements. The configuration of FIG. 6 is capable of reading each of the 96 wells of a conventional 96 well plate in just a few milliseconds without any opto-mechanical or electronic disturbance. The manifold is very rugged and highly reliable, making it suitable for portable laboratory equipment.

Figure 7:
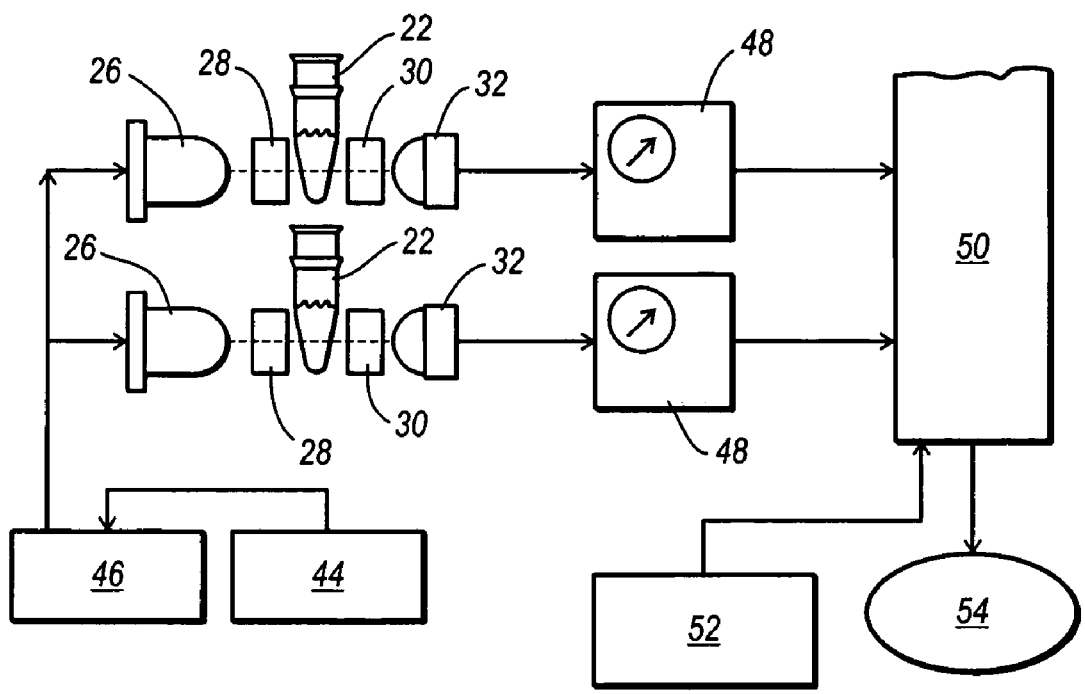
FIG. 7 is a schematic depicting an embodiment of a controller in connection with an optical manifold, sample holder and photo receiver.

FIG. 7 depicts schematically an embodiment of a controller system. DC power supply 44 is provided to power the plurality of excitation sources 26. One or more relays 46 are provided to operate each of a plurality of excitation sources 26. A computer or programmable logic controller (not shown), or other controller, turn the excitation sources on and off as desired. A single relay 46 may be used in some configurations to activate all of the excitation sources simultaneously, or separate relays may be used for each of the excitation sources.

A schematic representation of the optical excitation components is also shown in FIG. 7 using the same reference numerals assigned above with respect to various components: excitation sources 26 are shown in conjunction with excitation bandpass filters 28 so as to direct excitation light into sample vials 22. Emission bandpass filters 30 and photo receivers 32 receive fluorescent emission light from the samples. Data from the photo receivers is preferably passed to respective amplifiers 48, which amplify the signals from the corresponding photo receiver. It is contemplated that a typical photo receiver will produce an analog signal, and in such a case it is preferred that each amplifier have an adjustable gain so that a calibration may be performed to insure that each photo receiver/amplifier combination provide comparable data for subsequent analysis, thereby allowing for differences that may exist among system components under calibration conditions.

The signals from amplifiers 48 are sent to a multiplexing device 50, which operates in coordination with clocking device 52 to control switching between the plurality of inputs from the various amplifiers, and sends a signal to an analog input 54 of a computer, wherein the term "computer" is used broadly to include use of a programmable logic controller or other structure capable of performing this function.

Figure 8:
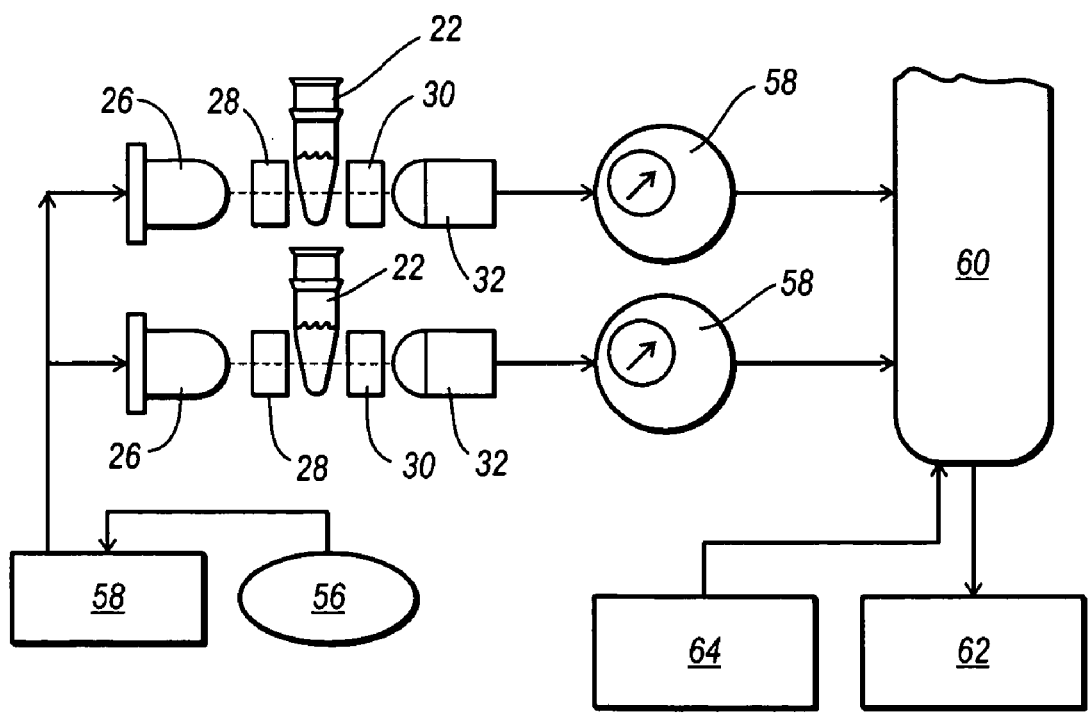
FIG. 8 is a schematic depicting another embodiment of a controller in connection with an optical manifold, sample holder and photo receiver.

FIG. 8 depicts another embodiment of a controller system, illustrating that various controller systems may be advantageously used in conjunction with the optical components described above. FIG. 8 shows an analog output 56 from a computer that is connected to an amplifier 58 used to drive excitation sources 26. LEDs used as excitation sources exhibit a brightness that is proportional to the applied voltage. This allows the computer or controller to control the intensity of LEDs used as excitation sources in response to needed sensitivity, or alternatively to account for calibration requirements. One method of calibration is to use a standardized fluorescent material in a known concentration and calibrating each channel until each channel produces the same measurement output. Various approaches can be used to perform this calibration: for example, one could separately adjust the gain of the amplifiers, or the intensity of the excitation source, or an adjustment may be handled at the computer.

In the embodiment of FIG. 8, it is preferred that the photo receivers be of the type typically referred to as "avalanche" receivers, which refers to receivers which change from a fully "off" state to a fully "on" state when the emitted luminosity of the fluorescing material reaches a certain level. The applied voltage required to cause the photo receiver to change to an "on" state can be used as a measure of the amount of fluorescence. For example, if a relatively large voltage (high intensity excitation source) is required to move the photo receptor to the "on" state, then only a small amount of fluorescence is occurring in the sample. The converse is true: if only a relatively small voltage results in activation of the photo receiver, this is an indication that a lot of fluorescence is occurring. Measurement of the voltage required to cause the photo receiver to change to the "on" state allows for quantitative determination of the amount of fluorescent material in the sample.

Non-linear amplifiers 58 may be used advantageously to amplify the signals from photo receivers 32. It is preferred that amplifiers 58 have variable gain adjustment ability to allow them to be more useful in a variety of circumstances. Shift register 60 is useful for monitoring one of the plurality of incoming signals to input 62 of the computer or controller. A digital "clock" signal 64 may be used in this configuration to cause shift register 60 to switch between the plurality of inputs from the various photo receivers so that all of the channels are read by the computer.

Figure 9:
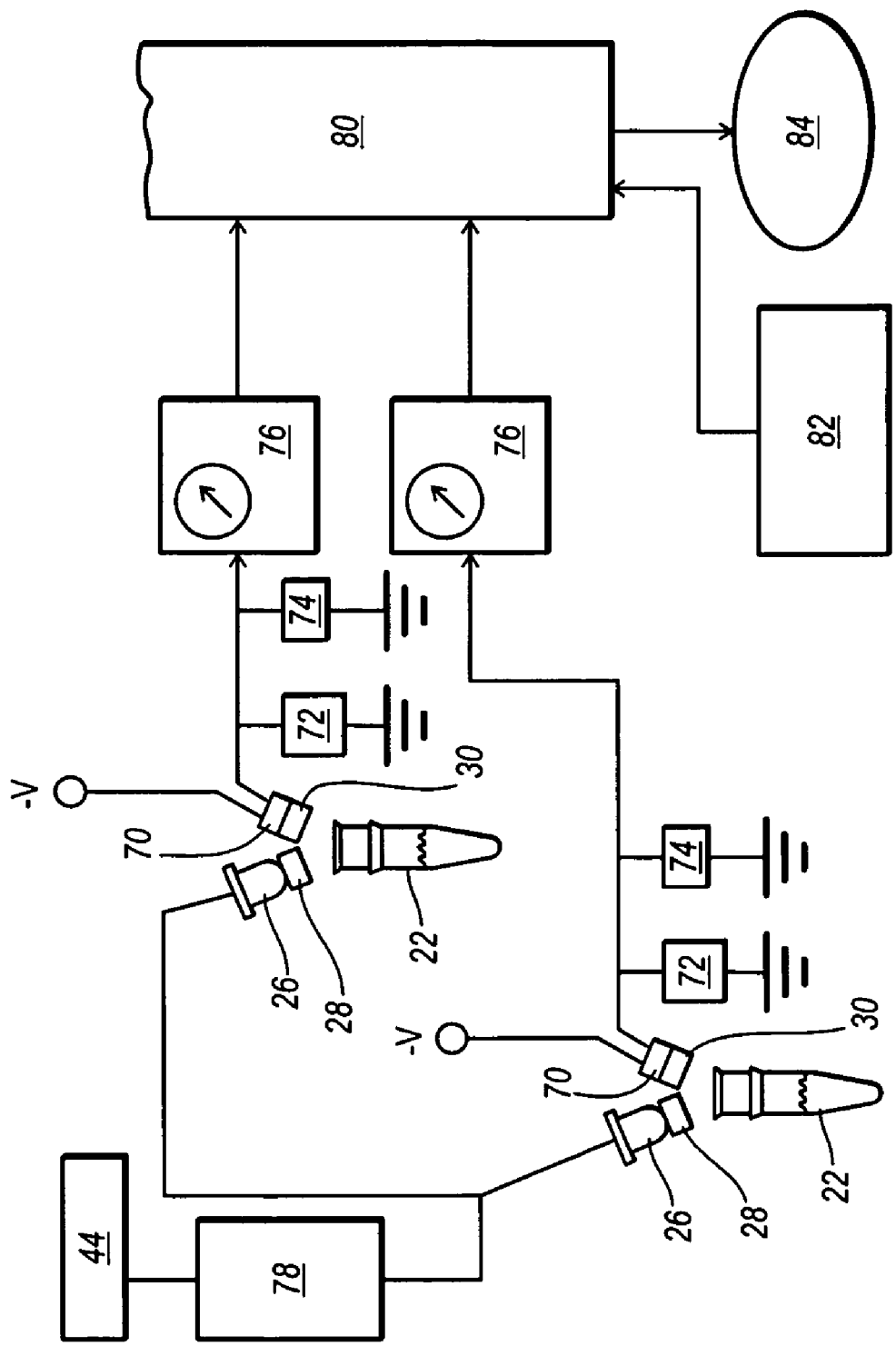
FIG. 9 is a schematic representation of an alternative embodiment of a detection system in accordance with the present invention.

FIG. 9 depicts schematically an embodiment of a high-gain low-noise electro-optical system. This system is shown with two sample vials 22, together with associated optical components, although it should be understood that a useful system might include only a single sample, or many samples.

Excitation sources 26 and excitation bandpass filters 28 are placed so as to direct excitation emissions onto a sample within sample vials 22. Emission bandpass filters 30 are shown in combination with photo resistors 70, which are sensitive photo resistors capable of creating high electronic gain from minute fluorescent photon emission sources. When using fluorescein as a fluorescent material, the preferred photo resistor is of a high impedance cadmium sulfide type which demonstrates good photo response for the fluorescein emission wavelength.

Associated with photo resistor 70 is a high impedance-dropping resistor 72, the combination of which allows a relatively large electrical signal to develop even in the presence of low light levels. Inclusion of filter capacitors 74 dampen electronic radio frequency (RF) interference by providing a shunting pathway to preclude amplification of RF electrical noise. Linear amplifiers 76 are provided with gain adjustment so as to permit the balancing of the plurality of electro-optical circuits with one another.

The electro-optical system of FIG. 9 is provided with a DC power supply 44 and a gating relay 78 controlled by a computer. The outputs of linear amplifiers 76 advantageously pass to an analog gating multiplexer 80, which in turn is connected to a digital gate signal 82 and an analog input 84 to a computer. The linear amplifiers also provide impedance matching with the analog gating multiplexer 80. The analog multiplexer provides a means whereby all of the outputs of the plurality of linear amplifier outputs can be sampled and read every few milliseconds by the managing computer, which is preferably a programmable logic controller for use with the embodiment of FIG. 9.

It has been discovered that use of a black opaque ultra low fluorescent sample vial allows for detection of lower level fluorescent emissions than a conventional clear sample vial. Without wishing to be bound by theory, it is believed that minute thermally induced changes in conventional clear vial walls contribute to variations in background fluorescence. Vials commonly found in the laboratory which are lightly pigmented for purposes of identification are also often highly fluorescent, which has been discovered to add noise and diminish sensitivity.

The embodiment of FIG. 9 provides similar photo sensitivity to that of a photo multiplier tube (PMT). It can sense small changes in very low light levels, and requires no mechanical stepping mechanism to read 96 sample vials containing fluorescent material in less than one second. Another advantage of this embodiment is that each photo resistor occupies a space of only about 9 mm by 9 mm, which is only a fraction of amount of space required for a PMT. Yet another advantage of this embodiment is that it uses low voltage, whereas a PMT typically requires voltages of 1000 volts or more.

Another advantage of the embodiment of FIG. 9 is the ability to use it in connection with monitoring of amplification using the polymerase chain reaction (PCR), by monitoring differences in fluorescence very early in the PCR process. In conventional systems, the first five PCR cycles are often considered to be the "zero" baseline because DNA growth cannot be successfully detected during these cycles. It is not until the 20th cycle before DNA amplification can be reliably observed in conventional systems due to noise. It has been found that the embodiment of FIG. 9 can detect positive DNA amplification between cycle 5 and cycle 7. For some applications, early detection of DNA amplification allows the use of fewer thermal cycles.

Figure 10:
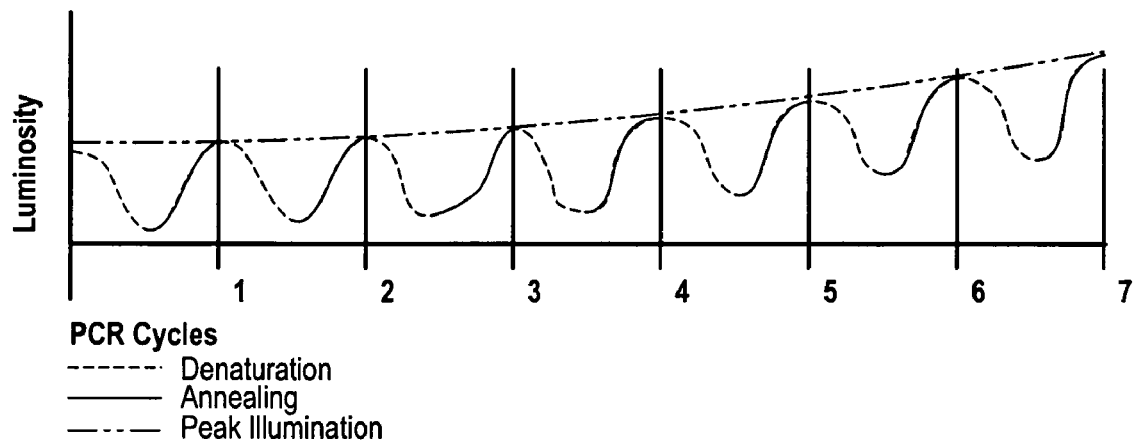
FIG. 10 depicts fluorescent luminosity during the first seven cycles of PCR.

FIG. 10 illustrates the luminescent output of a fluorescent probe which is at its highest level when DNA is double stranded, and its lowest level when the DNA is single stranded. The steady growth of double stranded DNA is indicated by the ever increasing illumination peaks at the end of the annealing phases. During the denaturation stage, the luminosity temporarily declines as all of the double stranded DNA is converted back to single stranded DNA. The luminosity returns and reaches an ever higher level as the successive annealing stages occur and more DNA is produced. This system allows for a definitive view of the rates of reaction of the biochemistry in the PCR process. Knowledge of the rate of reaction in the PCR process is very useful in prediction and optimization of the process.

More complex observations are also possible. For example, logarithmic curves of declining photo luminescence occurs during the denaturation portion of a PCR cycle. Reciprocally, a logarithmically increasing fluorescence is detected as the annealing takes place.

The sensitivity of the present invention may not be fully useful with traditional thermocyclers used in the practice of PCR, but the present invention is particularly useful in combination with the novel thermocyclers disclosed in copending patent application Ser. No. 10/991,746, entitled "Rapid Thermocycler," filed on Nov. 18, 2004, and having a common assignee with the present application, which application is incorporated herein in its entirety. This is because the transition times of conventional thermocyclers between different phases are typically about 45 seconds, and these extended transition times tend to obliterate or distort the observed curves. For better results, the transition time between phases should be reduced, preferably to only a few seconds. Conventional thermocyclers also suffer from significant thermal noise, which is reduced in the thermocyclers of the "Rapid Thermocycler" application.

Figure 11:
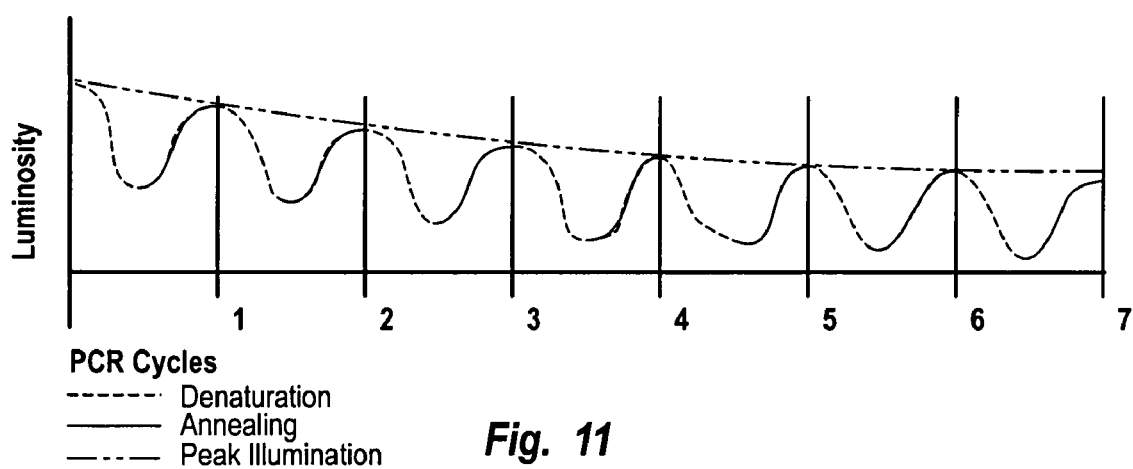
FIG. 11 depicts fluorescent luminosity during the first seven cycles of a PCR thermocycler in the absence of DNA amplification.

FIG. 11 illustrates PCR readings when no amplification takes place. The slope of the peaks is ever descending due to inherent decay of the fluorescent probe when exposed to constant illumination. This same decay is observed when exposing chemically pure fluorescein free of attachment to a probe. The decay rate is observed to be about 0.02% per second of continuous exposure to a strong source of excitation light. The fluorescent luminosity decay which is observed in this invention operates in opposition to growth in luminosity due to increases in DNA. This phenomenon serves to widen the differential luminescence between growth and no growth of DNA. During cycle one through cycle three the decay of the fluorescent signal may decrease the luminosity of the sample greater than the increase of luminosity associated with the growth in DNA. However in cycles 4 and above, the increase in luminosity associated with the growth in DNA will push the overall luminosity upward. After that, the binary nature of the DNA growth overwhelms the fluorescent signal decay.

Figure 12:
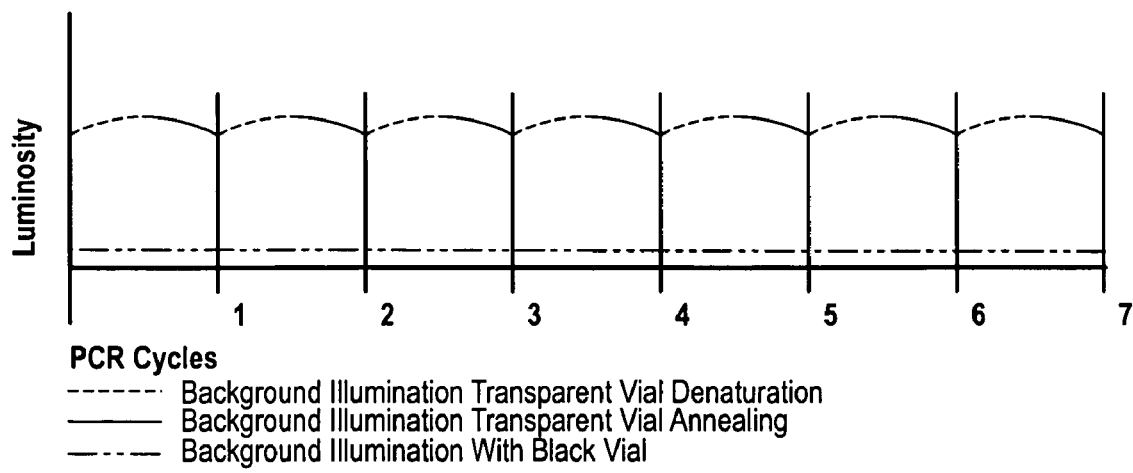
FIG. 12 shows fluorescent luminosity of noise during the first seven cycles of PCR using a conventional sample vial versus a black opaque PCR vial.

FIG. 12 compares the use of transparent thermoplastic vials and black opaque vials. The background signal of conventional clear sample vials can be almost totally eliminated by using a black opaque vial. When the background fluorescence is held to a minimum, the electro-optical signal can be more highly amplified as the signal-to-noise ratio is improved. Ultra-low fluorescent vials are very helpful in reducing noise for applications requiring detection of low level fluorescent changes.

Low level fluorescent detection is useful when qualitative PCR detection of potentially harmful biological agents is time sensitive. The amount of time required for statistically certain detection is reduced from nearly an hour or more when using conventional fluorescent PCR detection systems to 15 minutes or less when using the present invention in combination with the rapid thermocycler described in the copending application cited above.

The present invention provides an unusually useful and rapid fluorescent optical reader system, capable of reading every well of a 96 well plate in just a few milliseconds, without any moving parts, and without any opto-mechanical or electronic disturbance. The system provides an outstanding signal to noise ratio, which permits it to be used to differentiate between very low level differences in fluorescence. The inventive system is quite compact and sufficiently rugged to make it practical not only in laboratory applications but also in portable equipment intended for use in the field.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for detecting fluorescence, comprising:
a sample holder for holding a plurality of samples, at least some of which may contain a fluorescent material;
a plurality of excitation sources, one for each of the plurality of samples, capable of exciting the fluorescent material;
a plurality of photo receivers, one for each of the plurality of samples, capable of detecting fluorescent emissions from the fluorescent material when it is excited;
an emission bandpass filter for each of the plurality of photo receivers, each said emission bandpass filter being positioned perpendicular to the axis of reception of the photo receiver with which it is associated, with no further optical elements between the associated photo receiver and the associated sample;
an optical manifold for holding each excitation source and each photo receiver in association with the sample holder, so that operation of each excitation source will excite any of said fluorescent material within the corresponding sample and be detected by the corresponding photo receiver.

2. The system of claim 1, wherein each excitation source and corresponding photo receiver are offset off axis so as to fit in close proximity to one another while defining a ray trace from excitation source to the sample and back to the corresponding photo receiver.

3. The system of claim 1, wherein each excitation source and corresponding photo receiver are offset 7 degrees off axis.

4. The system of claim 1, further comprising an amplifier associated with each of the photo-receivers.

5. The system of claim 4, wherein each of the amplifiers are provided with an adjustable gain control.

6. The system of claim 1, wherein the illumination of the excitation source is proportional to the voltage applied, and further comprising a variable voltage control for each of the plurality of excitation sources.

7. The system of claim 1, wherein each of the photo receivers comprise an avalanche receiver.

8. The system of claim 1, further comprising a controller for passing data sequentially from the plurality of photo receivers to a recording device.

9. The system of claim 1, wherein the sample holder is configured to receive a plurality of sample vials.

10. The system of claim 1, wherein the sample holder contains a plurality of dimples for holding sample.

11. The system of claim 1, wherein the photo receivers comprise a high impedance cadmium sulfide photo resistor, and further comprising a high impedance dropping resistor for development of an electrical signal.

12. The system of claim 11, further comprising a filter capacitor for dampening electronic radio frequency interference.

13. A system for detecting fluorescence, comprising:
a sample holder for holding a plurality of samples;
a plurality of excitation sources, one for each of the plurality of samples;
a plurality of photo receivers, one for each of the plurality of samples;
an emission bandpass filter for each of the plurality of photo receivers, each said emission bandpass filter being positioned perpendicular to the axis of reception of the photo receiver with which it is associated, with no further optical elements between the associated photo receiver and the associated sample;

an optical manifold;

the optical manifold being configured for holding either the plurality of excitation sources or the plurality of photo receivers in association with the sample holder, and the sample holder being configured so as to hold the other of the plurality of excitation sources or the plurality of photo receivers, so that operation of each excitation source will excite any of said fluorescent material within the corresponding sample and be detected by the corresponding photo receiver.

14. The system of claim 13, wherein the optical manifold holds the plurality of excitation sources and the sample holder holds the plurality of photo receivers.

15. The system of claim 13, wherein the optical manifold holds the plurality of photo receivers and the sample holder holds the plurality excitation sources.

16. The system of claim 13, further comprising an amplifier associated with each of the photo-receivers.

17. The system of claim 16, wherein each of the amplifiers are provided with an adjustable gain control.

18. The system of claim 13, wherein the illumination of the excitation source is proportional to the voltage applied, and further comprising a variable voltage control for each of the plurality of excitation sources.

19. The system of claim 13, wherein each of the photo receivers comprise an avalanche receiver.

20. The system of claim 13, further comprising a controller for passing data sequentially from the plurality of photo receivers to a recording device.

21. The system of claim 13, wherein the sample holder is configured to receive a plurality of sample vials.

22. The system of claim 13, wherein the sample holder contains a plurality of dimples for holding sample.

23. The system of claim 13, wherein the photo receivers comprise a high impedance cadmium sulfide photo resistor, and further comprising a high impedance dropping resistor for development of an electrical signal.

24. The system of claim 13, further comprising a filter capacitor for dampening electronic radio frequency interference.

25. A system for detecting fluorescence, comprising:
a sample holder for holding a plurality of samples;
a plurality of excitation sources, one for each of the plurality of samples;
a plurality of photo receivers, one for each of the plurality of samples;
an emission bandpass filter for each of the plurality of photo receivers, each said emission bandpass filter being positioned perpendicular to the axis of reception of the photo receiver with which it is associated, with no further optical elements between the associated photo receiver and the associated sample;
the sample holder being configured for holding said plurality of excitation sources and plurality of photo receivers so that operation of each excitation source will excite any of said fluorescent material within the corresponding sample and be detected by the corresponding photo receiver.

26. The system of claim 25, wherein the photo receivers comprise a high impedance cadmium sulfide photo resistor, and further comprising a high impedance dropping resistor for development of an electrical signal.

27. The system of claim 25, further comprising a filter capacitor for dampening electronic radio frequency interference.

28. A method for detecting fluorescence in a plurality of samples, comprising: providing a plurality of samples including fluorescent material;
providing an excitation source for each of the plurality of samples for exciting said fluorescent material;
providing a photo receiver for each of the plurality of samples for detecting fluorescent emissions from said fluorescent material when it is excited;
providing an emission bandpass filter for each of the plurality of photo receivers, each said emission bandpass filter being positioned perpendicular to the axis of reception of the photo receiver with which it is associated, with no further optical elements between the associated photo receiver and the associated sample;
activating each excitation source; and
measuring the output of each photo receiver.

29. A system for detecting fluorescence as defined in claim 1, further comprising an excitation bandpass filter for each of the plurality of excitation sources, each said excitation bandpass filter being positioned perpendicular to the axis of emission of the excitation source with which it is associated, with no further optical elements between the associated excitation source and the associated sample.

30. A system for detecting fluorescence as defined in claim 1, wherein each excitation source has a corresponding photo receiver, and the axis of corresponding excitation source and its associated excitation bandpass filter is offset from the axis of the corresponding photo receiver and its associated emission bandpass filter by 180 degrees.

31. A system for detecting fluorescence as defined in claim 29, wherein each excitation source has a corresponding photo receiver, and the axis of corresponding excitation source and its associated excitation bandpass filter is offset from the axis of the corresponding photo receiver and its associated emission bandpass filter by 180 degrees.

32. A system for detecting fluorescence as defined in claim 13, further comprising an excitation bandpass filter for each of the plurality of excitation sources, each said excitation bandpass filter being positioned perpendicular to the axis of emission of the excitation source with which it is associated, with no further optical elements between the associated excitation source and the associated sample.

33. A system for detecting fluorescence as defined in claim 25, further comprising an excitation bandpass filter for each of the plurality of excitation sources, each said excitation bandpass filter being positioned perpendicular to the axis of emission of the excitation source with which it is associated, with no further optical elements between the associated excitation source and the associated sample.

34. A method for detecting fluorescence as defined in claim 28, further comprising the step of providing an excitation bandpass filter for each of the plurality of excitation sources, each said excitation bandpass filter being positioned perpendicular to the axis of emission of the excitation source with which it is associated, with no further optical elements between the associated excitation source and the associated sample.

* * * * *